United States Patent [19]

Richter et al.

[11] Patent Number: 4,487,928
[45] Date of Patent: Dec. 11, 1984

[54] PROCESS FOR THE PREPARATION OF POLYISOCYANATES CONTAINING ISOCYANURATE GROUPS, AND THE USE OF THE PRODUCTS OF THE PROCESS AS ISOCYANATE COMPONENT IN THE PRODUCTION OF POLYURETHANES

[75] Inventors: Roland Richter, Leverkusen; Hanns P. Müller, Odenthal; Kuno Wagner, Leverkusen, all of Fed. Rep. of Germany

[73] Assignee: Bayer Aktiengesellschaft, Leverkusen, Fed. Rep. of Germany

[21] Appl. No.: 333,943

[22] Filed: Dec. 23, 1981

[30] Foreign Application Priority Data

Jan. 8, 1981 [DE] Fed. Rep. of Germany ....... 3100262

[51] Int. Cl.$^3$ ................ C07D 251/34; C08G 73/06; C08G 18/28; C08G 18/70
[52] U.S. Cl. .................. 544/193; 544/222; 524/100; 528/423; 528/73
[58] Field of Search .............. 544/193, 222; 528/73, 528/423; 524/100

[56] References Cited

U.S. PATENT DOCUMENTS

| 2,952,665 | 9/1960 | Bunge | 260/77.5 |
|---|---|---|---|
| 3,252,942 | 5/1966 | France et al. | 260/77.5 |
| 3,330,828 | 7/1967 | Grogler et al. | 260/248 |
| 3,394,111 | 7/1968 | Liebsch | 260/77.5 |
| 3,622,577 | 11/1971 | Pederson | 260/248 |
| 3,686,225 | 8/1972 | Pederson | 260/340.3 |
| 3,919,218 | 11/1975 | Schmitt | 260/248 |
| 4,115,373 | 9/1978 | Henes et al. | 528/48 |
| 4,196,289 | 4/1980 | Seito et al. | 544/221 |
| 4,252,923 | 2/1981 | König et al. | 525/452 |
| 4,255,569 | 2/1981 | Mueller et al. | 544/193 |

FOREIGN PATENT DOCUMENTS

| 0010589 | 8/1979 | European Pat. Off. |
| 1013869 | 8/1957 | Fed. Rep. of Germany |
| 809809 | 11/1957 | United Kingdom |
| 952931 | 5/1962 | United Kingdom |
| 966338 | 8/1964 | United Kingdom |
| 1244416 | 9/1971 | United Kingdom |
| 1285367 | 8/1972 | United Kingdom |

OTHER PUBLICATIONS

J. H. Saunders & K. C. Frisch, Polyurethanes, Chemistry and Technology, pp. 94 et seq., (1962).
A. Farkas & G. A. Mills, Advances in Catalysis, vol. 13, 393, (1962).
Houben–Weyl, vol. 8, p. 244, publishers Thieme–Verlag.
J. G. Kresta, R. J. Chang, S. Kathiriya & K. C. Frisch, Makromol. Chem. 180, 1081, (1979).
Patent Abstracts of Japan, Band 2, NR 122, 13/10/78–Seite 2441C78 JPA 53-87379.
J. Amer. Chem. Soc. 89, 7017, (1967), Pendersen, Cyclicpolyethers.

*Primary Examiner*—John M. Ford
*Attorney, Agent, or Firm*—Gene Harsh; Joseph C. Gil; Thomas W. Roy

[57] ABSTRACT

The present invention thus relates to a process for the preparation of polyisocyanates having isocyanurate groups by the trimerization of part of the isocyanate groups of organic polyisocyanates or of mixtures of di- and mono-isocyanates in the presence of basic compounds as trimerization catalysts, with termination of the trimerization reaction by the addition of a catalyst poison, characterized in that the trimerization catalysts used are 1:1-complexes of (i) basic sodium or potassium compounds and (ii) 1,4,7,10,13-pentaoxacylopentadecane or 1,4,7,10,13,16-hexaoxacyclooctadecane.

This invention also relates to solutions suitable as catalyst components for this process, comprising 1:1-complexes of (i) basic sodium or potassium compounds and (ii) 1,4,7,10,13-pentaoxacyclopentadecane or 1,4,7,10,13,16-hexaoxacyclooctadecane dissolved in polar lacquer solvents and/or at least one compound within the molecular weight range of about 32 to 250 which has alcoholic hydroxyl groups and is liquid at room temperature.

This invention also relates to the use of the products of the process according to the invention, optionally freed from monomeric starting polyisocyanate and/or optionally blocked with blocking agents for isocyanate groups, as an isocyanate component in the production of polyurethanes by the isocyanate polyaddition process.

4 Claims, No Drawings

PROCESS FOR THE PREPARATION OF POLYISOCYANATES CONTAINING ISOCYANURATE GROUPS, AND THE USE OF THE PRODUCTS OF THE PROCESS AS ISOCYANATE COMPONENT IN THE PRODUCTION OF POLYURETHANES

BACKGROUND OF THE INVENTION

1. Field of the Invention

This invention relates to a new process for the preparation of polyisocyanates containing isocyanurate groups by the partial trimerization of the isocyanate groups of organic polyisocyanates or of mixtures of di- and mono-isocyanates, a catalyst solution suitable for carrying out this process, and the use of the products of the process as an isocyanate component in the production of polyurethanes by the isocyanate-polyaddition process.

2. Description of the Prior Art

Processes for the trimerization of organic isocyanates, in particular of polyisocyanates, are known in large numbers, (J. H. Saunders and K. C. Frisch, Polyurethanes Chemistry and Technology, page 94 et seq (1962)). Strong organic bases are suitable catalysts for this trimerization, e.g. those metal salts of carboxylic acids which are alkaline in reaction, metal alcoholates, metal phenolates, alkali metal carbonates, tert. amines, tert. phosphines and the "onium" compounds of nitrogen and phosphorus, and basic heterocyclic compounds of these elements. The catalysts are frequently used as combinations or together with other cocatalysts such as mono-N-substituted carbamic acid esters (A. Farkas and G. A. Mills, Advances in Catalysis, Vol. 13, 393 (1962)).

Most processes for the preparation of high quality polyisocyanates containing isocyanurate groups use expensive catalyst systems since it is known that simple metal salts such as carboxylates or alcohols are only capable of effecting cyclotrimerization of isocyanates at relatively high concentrations and at a high temperature; the trimerization of 5 parts of phenylisocyanate, for example, requires 1 part of potassium acetate and heating for 3 hours at 100° C. (Houben-Weyl, Vol. 8, page 244, publishers Thieme Verlag) (see also British Pat. No. 809,809, Example 6).

If trimerization with metal salts is to be carried out in solvents, highly polar aprotic solvents such as dimethyl formamide or dimethylsulphoxide must be used because only these are capable of dissolving inorganic metal salts and metal salts with a small organic group (German Offenlegungsschrift No. 2,839,084). Even then, catalyst concentrations of as much as 0.1 to 0.5% by weight are required. This also applies when the solvents used are protic but form urethanes with the isocyanate, thereby lowering the isocyanate content, or form precipitates and cloudiness so that the reaction product must be filtered (British Pat. No. 920,080).

Furthermore, the metal salts known in the art effect rapid trimerization only in the case of aromatic isocyanates while aliphatic mono- and polyisocyanates require a high catalyst concentration and temperatures above 50° C., whereby the reaction frequently takes an uneven exothermic course and in the case of polyisocyanates results in highly viscous, strongly discolored products (see U.S. Pat. No. 3,330,828, Examples 1 to 4; British Pat. No. 952,931, Example 3; German Auslegeschrift No. 1,013,869, Example 3) or the formation of gel particles (British Pat. No. 966,338, Example 3), whereby the products become to a large extent unsuitable for use in polyurethane lacquers. Another major disadvantage of using metal salts as catalysts is that stopping the catalyst results in the formation of inorganic salts which are insoluble in the polyisocyanate and cause cloudiness. The more recent processes of the art therefore rarely use the simple and inexpensive basic metal salts such as potassium acetate but special organic bases, depending on the particular isocyanate, and these are used under quite specific reaction conditions. Thus, for example, the trimerization of aromatic polyisocyanates is carried out using Mannich bases (German Offenlegungsschrift No. 2,551,634 and German Offenlegungsschrift No. 2,641,380) or tertiary phosphines, in which case uretdiones are first formed which are converted to the isocyanurate only in a second phase of the reaction (German Offenlegungsschrift No. 1,201,992). Organic bases having a betaine structure, such as quaternary ammonium hydroxides (European Offenlegungsschrift No. 010,589 and European Offenlegungsschrift No. 009,694), aminimides (J. E. Kresta, R. J. Chang, S. Kathiriya and K. C. Frisch, Makromol. Chem. 180, 1081 (1979)) and azirine derivatives in combination with tert. amines (German Auslegeschrift No. 2,325,826) are frequently used for the trimerization of (cyclo)aliphatic diisocyanates.

One disadvantage of all these catalyst systems is that quite specific temperature intervals must be observed and the process may in part only be carried out solvent-free and in part only in selected solvents, and in particular trimerization can only be carried out on aromatic polyisocyanates alone or aliphatic polyisocyanates alone.

It is an object of the present invention to provide a process by which colorless aromatic and aliphatic polyisocyanates containing isocyanurate groups may be obtained by a technically simple procedure either in solvents or solvent-free and without elaborate temperature control, using one and the same catalyst.

It was surprisingly found that this problem could be solved by carrying out the trimerization using 1:1-complexes of basic sodium or potassium compounds with 1,4,7,10,13-pentaoxacyclopentadecane ("15-crown-5") or 1,4,7,10,13,16-hexaoxacyclooctadecane ("18-crown-6") as trimerization catalysts.

Although C. J. Pedersen already recognized that crown-ether-complexed alkali metal salts are fundamentally suitable as trimerization catalysts for aromatic isocyanates (J. Am. Chem. Soc. 89, 7017 (1967) or U.S. Pat. No. 3,686,225), the crown ethers containing condensed benzene or cyclohexane rings described in these prior publications and their complexes with basic sodium or potassium compounds are not suitable for large scale technical production of high quality polyisocyanates containing isocyanurate groups, firstly because the crown ethers with condensed cyclohexane rings have only an extremely slight complex forming action on basic alkali metal compounds and, secondly, because 1:1 complexes based on crown ethers having condensed benzene rings have very poor solubility in organic media so that, for example, concentrated catalyst solutions in physiologically harmless solvents cannot be prepared using these complexes. By contrast, the 1:1 complexes described below which are to be used in the process according to the invention do not have such disadvantages. The crown ethers underlying the 1:1 complexes which are an essential feature of this invention are eminently suitable for the preparation of stable complexes with basic sodium and potassium compounds and at the same time these complexes are readily soluble both in the polyisocyanates to be trimerized and in the auxiliary solvents which will be described below. They may therefore be added as relatively concentrated solutions to the trimerizing polyisocyanate, a factor which is important for the large scale technical production of polyisocyanates having isocyanurate groups.

SUMMARY OF THE INVENTION

The present invention thus relates to a process for the preparation of polyisocyanates having isocyanurate groups by the trimerization of part of the isocyanate groups of organic polyisocyanates or of mixtures of di- and mono-isocyanates in the presence of basic compounds as trimerization catalysts, with termination of the trimerization reaction by the addition of a catalyst poison, characterized in that the trimerization catalysts used are 1:1-complexes of (i) basic sodium or potassium compounds and (ii) 1,4,7,10,13-pentaoxacyclopentadecane or 1,4,7,10,13,16-hexaoxacyclooctadecane.

This invention also relates to solutions suitable as catalyst components for this process, comprising 1:1-complexes of (i) basic sodium or potassium compounds and (ii) 1,4,7,10,13-pentaoxacyclopentadecane or 1,4,7,10,13,16-hexaoxacyclooctadecane dissolved in polar lacquer solvents and/or at least one compound within the molecular weight range of about 32 to 250 which has alcoholic hydroxyl groups and is liquid at room temperature.

This invention also relates to the use of the products of the process according to the invention, optionally freed from monomeric starting polyisocyanate and/or optionally blocked with blocking agents for isocyanate groups, as an isocyanate component in the production of polyurethanes by the isocyanate polyaddition process.

DETAILED DESCRIPTION OF THE INVENTION

In the context of this invention, the term "1:1-complexes" is used to denote complexes of equimolar quantities of a basic sodium or potassium compound with 15-crown-5 or 18-crown-6. Complex formation of the sodium compound is carried out using the first mentioned cyclic polyether while complex formation of the potassium compound is carried out with the last mentioned cyclic polyether.

The basic sodium or potassium compounds used according to the invention may be any compounds of the aforesaid alkali metals whose aqueous solution at a 1 molar concentration has a pH of at least about 7.5. Suitable basic compounds are, for example, sodium or potassium carboxylates preferably having 1-12 carbon atoms, alcoholates preferably having 1-8 carbon atoms, phenolates preferably having 6-10 carbon atoms, carbonates, hydroxides, cyanates, enolates or cyanides. Suitable basic sodium or potassium compounds are, for example, the formates, acetates, propionates, 2-ethylhexanoates, n-dodecanoates, caprylates, methylates, ethylates, butylates, hexylates, phenolates, tert.-butylphenolates, carbonates, hydroxides, cyanates, thiocyanates or cyanides of the above-mentioned metals or also, for example, sodium- or potassium-N-methylacetamide. Included among the preferred basic compounds are the aforementioned carboxylates, alcoholates, phenolates, carbonates, hydroxides, cyanates and cyanides. Particularly preferred are simple carboxylates of the above-mentioned alkali metals having 1-4 carbon atoms, in particular potassium acetate.

The cyclic polyethers used for complex formation are known compounds. Their preparation may be carried out, for example, according to G. Johns, C. J. Ransom, C. B. Reese, Synthesis (1976), page 515.

The preparation of the 1:1-complexes to be used in the process according to the invention may be carried out, for example, according to one of the following methods:

1. Preparation is carried out using the polyisocyanate which is to be trimerized or its solution in a suitable solvent which may also serve as reaction medium for carrying out the process according to the invention, so that the cyclic polyether is dissolved in the polyisocyanate or its solution, and the alkali metal salt is stirred in as a solid, with complex formation and solution.

2. The cyclic polyether is dissolved in a suitable solvent, and the alkali metal salt is then added with complex formation and solution. Any cloudiness is removed by filtration.

3. The procedure is as described under 2. but using a relatively volatile solvent which is drawn off after complex formation so that the complex precipitates as solid residue which is subsequently dissolved in another solvent and/or in the polyisocyanate to be trimerized.

When preparing the 1:1-complexes, components (i) and (ii) are preferably used in equimolar quantities. It would, of course, be possible to operate with different quantitative proportions, but either the basic alkali metal compound or the cyclic polyether would then be present in excess. As will readily be seen, such a procedure would hardly be suitable since the excess would have little or no catalytic activity. When preparing solutions of 1:1-complexes, components (i) and (ii) are generally used in quantities such that the complexes are present as about 0.4 to 40% by weight, preferably about 0.8 to 20% by weight solutions. It is precisely one of the main advantages of the catalysts which are essential to this invention that they are soluble at such comparatively high concentrations in the solvents mentioned as examples below.

Solvents which, as indicated above, may also be used as reaction media for the preparation of the complexes are in particular the usual polar, physiologically substantially harmless solvents used in polyurethane lacquer technology, which have a boiling point from about 50° C. to 350° C. at normal pressure, or compounds containing alcoholic hydroxyl groups which are liquid at room temperature and have a molecular weight from about 32 to 250, preferably from about 46 to 162. Any mixtures of such solvents may, of course, also be used. Examples of suitable lacquer solvents of the above-mentioned type are: ethyl acetate, butyl acetate, ethyl glycol acetate, acetone, methyl ethyl ketone, methyl isobutyl ketone, cyclohexanone, methoxyhexanone or also chlorinated hydrocarbons such as, for example, chloroform or chlorobenzene. With diluents such as toluene, xylene and higher aromatic compounds, for example, there is only limited solubility. Larger additions of such solvents may lead to cloudiness and precipitation. Examples of compounds with alcoholic hydroxyl groups which are suitable as solvents are: methanol, ethanol, isopropanol, ethylene glycol acetate, ethylene glycol, diethylene glycol, ethylene glycol monoethylether, glycerol or trimethylolpropane. Since the 1:1-complexes are generally very readily soluble in such compounds having hydroxyl groups so that these alcoholic solvents need only be used in very small quantities, their presence does not interfere with carrying out the process according to the invention.

In addition to the aforesaid solvents, however, higher boiling solvents may also be used, e.g. the usual plasticizers such as dibutylphthalate, butylbenzylphthalate or phosphoric acid esters such as tricresylphosphate.

Polyisocyanates suitable for carrying out the process according to the invention are in principle any organic polyisocyanates having aliphatically, cycloaliphatically, araliphatically, heterocyclically and/or aromatically bound isocyanate groups of the molecular weight range of about 140 to 300, such as e.g. tetramethylene diisocyanate, hexamethylene diisocyanate, 1-isocyanato-3,3,5-trimethyl-5-isocyanato-methyl-cyclohexane (isophorone diisocyanate, abbreviated: IPDI), the isomeric xylylene diisocyanates, 2,4- and/or 2,6-diisocyanato-toluene, or 2,4- and 4,4'-diisocyanato-diphenylmethane, and any mixtures of such polyisocyanates. Included among the preferred starting materials for the process according to the invention are 2,4-diisocyanato-toluene, 2,6-diisocyanato-toluene, any mixtures of these isomers, hexamethylenediisocyanate, IPDI, and any mixtures of these preferred diisocyanates. Particularly suitable are also mixtures of the last-mentioned diisocyanates having cycloaliphatically or aliphatically bound isocyanate groups with aromatic diisocyanates of the last-mentioned type in proportions by weight of about 1:3 to 3:1.

Isocyanate prepolymers having isocyanate groups, such as are obtained by the reaction of excess quantities of the diisocyanates exemplified above with compounds having isocyanate reactive groups, or also higher functional polyisocyanates, for example polyisocyanate mixtures such as are formed from the phosgenation of aniline/formaldehyde condensates, may in principle also be used as starting materials in the process according to the invention, although the use of such modified or higher functional polyisocyanates is less preferred. Mixtures of diisocyanates and monoisocyanates may in principle also be used as starting materials in the process according to the invention to result in interesting polyisocyanates having isocyanurate groups with the isocyanate functionality reduced by a controlled amount. In this case, the di- and mono-isocyanates are generally used in a molar ratio diisocyanate:monoisocyanate of about 1.5:1 to 2.5:1. Suitable monoisocyanates are, for example, aliphatic monoisocyanates having 1 to 18, preferably 4 to 8 carbon atoms, such as methyl isocyanate, n-butylisocyanate, n-octylisocyanate or stearylisocyanate or aromatic monoisocyanates such as in particular phenylisocyanate.

When carrying out the process according to the invention, only a portion of the isocyanate groups of the starting polyisocyanate is trimerized. This means that the trimerization reaction is stopped at a degree of trimerization (degree of trimerization=percentage of trimerized isocyanate groups, based on the total number of isocyanate groups originally present) of about 10 to 70%. If the process according to the invention is carried out in the presence of solvents so that the process products according to the invention are directly obtained as solutions which are used, as such, e.g. to serve as polyisocyanate components in lacquers, the trimerization reaction is preferably stopped at a trimerization degree of from about 50 to 70% in order to keep the proportion of completely unreacted starting isocyanate in the solutions as low as possible. If the process is carried out in the absence of solvents, in particular if the unreacted starting diisocyanate is to be removed after termination of the trimerization reaction, for example by thin layer distillation, the trimerization reaction is generally stopped at a degree of trimerization of about 10 to 50%, preferably about 20 to 40%.

Suitable catalyst poisons are, for example, acid chlorides such as benzoyl chloride, acetyl chloride, oxalyl chloride, succinic acid dichloride, terephthalic acid dichloride, 2,5-dichlorobenzyl acid chloride, phosphorus trichloride or thionyl chloride or strong acids such as p-toluene sulphonic acid, nonafluorobutanesulphonic acid or phosphoric acid as well as carbamic acid chlorides such as may be formed by the addition of HCl to isocyanates, which inactivate the essential catalysts of the invention with neutralization of the basic alkali metal compounds.

Preparation of the polyisocyanates containing isocyanate groups may be carried out solvent-free or in the presence of suitable solvents. Suitable solvents are in particular the lacquer solvents already mentioned above as examples, which have no isocyanate reactive groups.

The process according to the invention is generally carried out in the temperature range of about 0° to 80° C., preferably about 20° to 60° C. The catalyst quantity to be used depends on the nature of the starting polyisocyanate and is generally at about 0.001 to 1.0% by weight, preferably about 0.003 to 0.5% by weight, based on the weight of the 1:1-complex and the weight of the starting polyisocyanate. The particularly preferred range in the case of aromatic starting polyisocyanates is about 0.003 to 0.05% by weight and in the case of aliphatic starting polyisocyanates is about 0.03 to 0.5% by weight.

The method of adding the catalyst may be carried out by various methods as may the preparation of the catalyst already described above:

1. When the catalyst is prepared in the starting polyisocyanates as already mentioned under 1. above, the trimerization reaction starts spontaneously after formation of the complex. In this variation, the individual components of the complex are therefore added separately to the starting polyisocyanate.

2. The catalyst may in principle also be incorporated in a solid form with the starting polyisocyanate.

3. The catalyst is preferably added in the form of the above described solutions in the lacquer solvents exemplified above and/or in the compounds with alcoholic hydroxyl groups exemplified above. Such solutions of the 1:1-complexes which are particularly suitable for the process according to the invention generally have a solid content of about 0.4 to 40, preferably about 0.8 to 20% by weight.

If the process according to the invention is carried out in the presence of one of the lacquer solvents exemplified above, it may often be advisable to dispense with separation of the solvent and use the solution of the process products in the above-mentioned solvents directly for the preparation of polyurethane products, for example for the preparation of polyurethane lacquers. In such a case, the same solvent is preferably used both for the 1:1-complex which is essential to the invention and for the reaction medium, the quantity of which solvent is calculated so that solutions of the process products according to the invention have a solid content of about 20 to 80, preferably about 40 to 60% by weight.

After addition of the catalyst, for example at room temperature, the trimerization reaction starts up spontaneously, both in the case of starting isocyanates having aliphatic isocyanate groups and those having aromatic isocyanate groups, and both in the presence of solvents and in their absence. When using the optimally active quantity of the essential catalyst of the invention, which can be determined by a simple investigative preliminary test, the reaction temperature generally rises to about 30°–60° C. so that as a result of the careful trimerization reaction, a colorless, clear reaction product is obtained after a period of about 1 to 8 hours. When the maximum temperature has been reached, no additional heating need be applied to the reaction mixture but it may be advantageous to maintain the reaction temperature within the range of about 40° to 50° C. by heating or cooling in order to observe the optimum reaction times.

When the desired degree of trimerization has been reached, the reaction is stopped by the addition of one of the catalyst poisons exemplified above. For complete termination of the trimerization reaction, it is generally sufficient to add an at least equimolar quantity of the catalyst poison, based on the 1:1-complex. After termination of the trimerization reaction, the reaction mixture may, if desired, be worked up by distillation. Thus, for example, the amount of excess starting polyisocyanate in the process products may be reduced to below about 3% by weight, preferably below about 0.7% by weight, by its removal in a thin layer evaporator.

The process according to the invention has the following advantages over the known art:

1. The catalyst system which is essential to the invention is suitable for the trimerization of both aromatic and aliphatic polyisocyanates, and the reaction may be carried out as a slightly exothermic reaction at a low reaction temperature so that the risk of impairing the quality of the process products by high temperatures can be virtually excluded.
2. The quantity of catalyst is invariably less than in the known processes of the state of the art, in particular in the case of aromatic starting polyisocyanates.
3. The trimerization velocity is so high that the reaction may generally be carried out without external supply of energy.
4. The catalysts may also be spontaneously inactivated at the low temperature range of about 20° to 60° C., whereby discolorations of the process products such as can be observed in case of thermal inactivation are eliminated.
5. Due to the inactivation of the catalyst, the formation of insoluble inorganic salts which cause cloudiness, as is normally the case when using metal compounds does not occur, and the neutral salts formed remain in solution due to the complex forming effect of the crown ethers, so that clear, colorless end products are formed.
6. The process products according to the invention are stable in storage and by-products such as uretdiones or carbodiimides are not formed.

The process products according to the invention are valuable raw materials for the production of polyurethanes by the isocyanate polyaddition process. They are suitable in particular as isocyanate components in two-component polyurethane lacquers. For this purpose they may also be used in a masked form, masked with blocking agents for isocyanate groups. Another important field of application for the process products according to the invention is their use as cross-linking agents for adhesives based on at least one high molecular weight compound containing isocyanate reactive hydrogen atoms(s).

The percentages mentioned in the following examples are percentages by weight.

EXAMPLE 1

0.05 ml of a 0.2 molar solution of potassium acetate/18-crown-6 in diethylene glycol monomethylether (0.0036% total catalyst concentration) are added to 100 g of a mixture of 65% by weight 2,4- and 35% by weight 2,6-tolylene diisocyanate at 40° C. Trimerization sets in at once with heating, a maximum temperature of 56° C. being reached. After 15 minutes stirring, the isocyanate content is 38.8%. The reaction is stopped by the addition of 0.05 ml of a 0.2 molar solution of benzoyl chloride in diethylene glycol dimethylether and the mixture is stirred for a further 30 minutes at 40° C.

EXAMPLE 2

100 g of 2,4-tolylenediisocyanate are dissolved in 100 g of anhydrous butyl acetate, and 0.35 ml of a 0.1 molar solution of potassium acetate/18-crown-6 in 2-ethylhexanol (0.013% total catalyst concentration) are added with stirring at 40° C. Trimerization sets in at once, the temperature rising only minimally (42° C.). After 16 hours, 35 minutes stirring at 40° C., the isocyanate content has fallen to 7.9%. The reaction is stopped by the addition of 0.01 ml of nonafluorobutanesulphonic acid and the mixture is stirred for a further 15 minutes at 60° C. The clear, colorless solution contains 0.53% of free tolylene diisocyanate (based on the solid content) and has a viscosity of 3054 mPas (25° C.).

EXAMPLE 3

100 g of 2,4-tolylene diisocyanate are dissolved in 100 g of anhydrous butyl acetate, and 5 ml of a 0.01 molar solution of potassium acetate/18-crown-6 in butyl acetate (0.018% total catalyst concentration) are added with stirring at room temperature. Trimerization sets in at once with heating, a maximum temperature of 57° C. being reached. After 8 hours, 20 minutes stirring without additional heating, the isocyanate content has fallen to 8.9%. The reaction is stopped by the addition of 0.007 g of benzoyl chloride and the mixture is stirred for a further 10 minutes. The clear, colorless solution contains 0.043% of free tolylene diisocyanate (based on a 100% product) and has a viscosity of 2390 mPas (25° C.).

EXAMPLE 4

1044 g (6 mol) of 2,4-tolylene diisocyanate are dissolved in 1000 g of anhydrous butyl acetate, and 60 ml of a 0.01 molar solution of potassium acetate/18-crown-6 in butyl acetate (0.021% total catalyst concentration) are added with stirring at room temperature. Trimerization sets in at once with heating, a maximum temperature of 60° C. being reached after 2 hours. After a further 3 hours stirring without additional heating, the isocyanate content is 9.0%. The viscous solution is then divided into 10 samples of about 208 g each, and these samples are stopped with 0.06 mMol of, respectively, benzoyl chloride, phosphoric acid, thionyl chloride, phosphorus trichloride, acetyl chloride, oxalyl chloride, succinic acid dichloride, terephthalic acid dichloride, 2,5-dichlorobenzoic acid chloride (Sample 10 without stopper). After 2 months, the isocyanate content of all nine samples is 9.0%. In Sample 10 (without stopper), the isocyanate content has fallen to 7.3% NCO within the same length of time.

EXAMPLE 5

3 ml of a 0.01 molar solution of potassium acetate/18-crown-6 in butyl acetate (0.015% total catalyst concentration) are added to 100 g of a mixture of 65% by weight 2,4- and 35% by weight 2,6-tolylene diisocyanate at room temperature. Trimerization sets in at once with heating, a maximum temperature of 79° C. being reached. After 25 minutes stirring, the isocyanate content is 32.7%. The reaction is stopped by the addition of 0.0035 ml benzoyl chloride and the mixture is stirred for a further 10 minutes.

EXAMPLE 6

0.46 g (0.091%) of a preformulated, crystalline complex of potassium acetate and 18-crown-6 are added at room temperature to 504 g (3 mol) of hexamethylene diisocyanate with stirring. The weakly exothermic trimerization (maximum temperature 37° C.) sets in at once. After 3 hours, 35 minutes, the isocyanate content is 42%. The reaction is stopped by the addition of 0.15 ml benzoyl chloride and the mixture is stirred for a further 15 minutes. The slightly yellowish solution is filtered (part of the complex remains insoluble in HDI). After thin layer distillation, 125 g of a pale yellowish product is obtained. Isocyanate content: 22.3%, viscosity (25° C.): 1949 mPas, monomeric HDI content: <0.1%.

The results of gel chromatography are: 63% monoisocyanurate and 35% higher molecular weight polyisocyanates with isocyanurate structure.

EXAMPLE 7

1.53 ml of a 0.5 molar solution of potassium acetate/18-crown-6 in diethylene glycol monomethylether (0.055% total catalyst concentration) are added to 504 g (3 mol) of hexamethylene diisocyanate with stirring at room temperature. The exothermic trimerization (maximum temperature 58° C.) sets in at once. After 45 minutes. The isocyanate content of the solution is 40.8%. The reaction is stopped by the addition of 5 mg of nonafluorobutanesulphonic acid and the mixture is stirred for a further 15 minutes. After thin layer distillation without previous filtration, 140 g of a clear, almost colorless product is obtained. Isocyanate content: 23%, viscosity (25° C.): 2375 mPas, free monomeric HDI content: <0.1%.

EXAMPLE 8

5 ml of a 0.1 molar solution of potassium acetate/18-crown-6 in 2-ethylhexanol (0.036% total catalyst system concentration) are added to 504 g (3 mol) of hexamethylene diisocyanate with stirring at room temperature. The weakly exothermic trimerization sets in at once (maximum temperature 36° C.). After 4 hours 30 minutes, the isocyanate content of the solution is 40.6%. The reaction is stopped by the addition of 0.012 ml benzoyl chloride and the mixture stirred for a further 15 minutes. Thin layer distillation of the clear solution yields 180 g of a clear, slightly yellowish product. Isocyanate content: 22.9%, viscosity (25° C.): 2653 mPas, free monomeric HDI content: <0.1%.

Although the invention has been described in detail in the foregoing for the purposes of illustration, it is to be understood that such detail is solely for that purpose and that variations can be made therein by those skilled in the art without departing from the spirit and scope of the invention except as it may be limited by the claims.

What is claimed is:

1. A process for the preparation of polyisocyanates containing isocyanurates groups which comprises trimerizing a part of the isocyanate groups of organic polyisocyanates or of mixtures of di- and mono-isocyanates in the presence of basic compounds as trimerization catalysts and terminating the trimerization reaction by the addition of a catalyst poison, characterized in that said trimerization catalysts are 1:1-complexes of (i) potassium carboxylates having 1 to 4 carbon atoms and (ii) 1,4,7,10,13,16-hexaoxacyclooctadecane.

2. The process according to claim 1 wherein said trimerization catalyst is a 1:1-complex of potassium acetate and 1,4,7,10,13,16-hexaoxacyclooctadecane.

3. The process according to claim 1 or 2, wherein said 1:1-complex is used in the form of a solution in a polar lacquer solvent and/or at least one compound of the molecular weight range of about 32 to 250 which has alcoholic hydroxyl groups and is liquid at room temperature.

4. A process for the preparation of polyurethanes which comprises
   (a) preparing polyisocyanates in accordance with the process of claim 1, or 2, and
   (b) reacting said polyisocyanate with at least one compound containing isocyanate-reactive hydrogen atom(s).

* * * * *